United States Patent [19]
Osipov

[11] Patent Number: 5,134,999
[45] Date of Patent: Aug. 4, 1992

[54] ULTRASONIC TRANSDUCER ASSEMBLY
[75] Inventor: Vladimir W. Osipov, Barre, Mass.
[73] Assignee: Walker Magnetics Group, Inc., Worcester, Mass.
[21] Appl. No.: 704,070
[22] Filed: May 22, 1991
[51] Int. Cl.⁵ .............................. A61B 8/00
[52] U.S. Cl. ..................... 128/661.03; 128/662.03
[58] Field of Search ......... 128/660.01, 661.03–661.05, 128/662.03–662.04, 661.02

[56] References Cited
U.S. PATENT DOCUMENTS

| | | | |
|---|---|---|---|
| 4,059,098 | 11/1977 | Murdock | 128/660.01 |
| 4,433,690 | 2/1984 | Green et al. | 128/661.02 |
| 4,774,959 | 10/1988 | Palmer et al. | 128/660.06 |
| 4,796,632 | 1/1989 | Boyd et al. | 128/662.03 |
| 4,976,267 | 12/1990 | Jeffcott et al. | 128/660.01 |
| 5,014,970 | 5/1991 | Osipov | 269/328 |
| 5,054,490 | 10/1991 | Rossman et al. | 128/661.03 |

Primary Examiner—Francis Jaworski
Attorney, Agent, or Firm—Henry D. Pahl, Jr.

[57] ABSTRACT

In the ultrasonic bone testing apparatus disclosed herein, a pair of ultrasonic transducer assemblies are brought into contact with opposite sides of a patient's foot and each of the transducer assemblies includes, as an acoustic waveguide, a liquid filled bladder. The foot engaging end of each bladder is formed as a laterally projecting rounded cone so that, as the transducer assemblies are brought into contact with the foot, air is progressively and totally excluded from an enlarging area of contact. One or both of the transducer assemblies can be scanned with a small circular motion so that a variety of locations of the patient's foot can be sampled and the response can be analyzed.

6 Claims, 3 Drawing Sheets

ULTRASONIC TRANSDUCER ASSEMBLY

BACKGROUND OF THE INVENTION

The present invention relates to ultrasonic bone testing and more particularly to an improved apparatus for coupling ultrasonic energy into and out of a patient's foot without requiring immersion of the patient's foot in a liquid.

It has previously been proposed to screen for osteoporosis and other degenerative bone diseases by transmitting ultrasonic energy of differing frequencies through the calcaneus in a patient's foot and by measuring the selective attenuation of energy by the bone. One particular apparatus for conducting such testing is disclosed in U.S. Letters Pat. No. 4,774,959 issued Oct. 4, 1988 to Stuart B. Palmer and Christian M. Langton and entitled Narrow Band Ultrasonic Frequency Attenuation Bone Measurement System. In the apparatus disclosed in that patent, a patient's foot is immersed in a liquid containing tank and the calcaneus is located between a pair of opposing transducers. As is understood by those skilled in the art, immersion in a liquid, particularly with a wetting agent included, is an effective way of coupling ultrasonic energy into and out of an irregularly shaped and surfaced object such as a human foot. For use as a general screening technique, however, the use of an immersing procedure is relatively time consuming and messy. On the other hand, the presence of air or other gas in between an ultrasonic transducer and an object to be tested will interfere with the coupling of ultrasonic energy and will lead to inconsistent measurements.

Among the several objects of the present invention may be noted the provision of ultrasonic bone testing apparatus which permits ultrasonic energy to be efficiently coupled into and out of an appropriate portion of a patient's body; the provision of such apparatus which facilitates the coupling of ultrasonic energy without requiring immersion; the provision of such apparatus which is useful for mass screening; the provision of such apparatus which is easy to operate; the provision of such apparatus which is relatively tolerant of patient positioning; the provision of such apparatus which permits testing to be conducted quickly; the provision of such apparatus which promotes reproducible measurements; the provision of such apparatus which is highly reliable and which is of relatively simple and inexpensive construction. Other objects and features will be in part apparent and in part pointed out hereinafter.

SUMMARY OF THE INVENTION

Briefly, ultrasonic bone testing apparatus in accordance with the present invention involves a footrest and a pair of ultrasonic transducer assemblies. One of the pair of transducer assemblies is mounted on each side of a foot positioned in the footrest, at least one of the transducer assemblies being movable laterally of the foot thereby to permit a foot to be initially placed in the footrest. Each of the transducer assemblies includes a transducer and an acoustic waveguide in the form of a liquid filled bladder. The foot engaging end of each bladder is in the form of a laterally projecting rounded cone. Accordingly, air can be progressively excluded from an enlarging area of contact with a foot in the footrest as the transducer assemblies are brought into contact with opposite sides of the foot.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
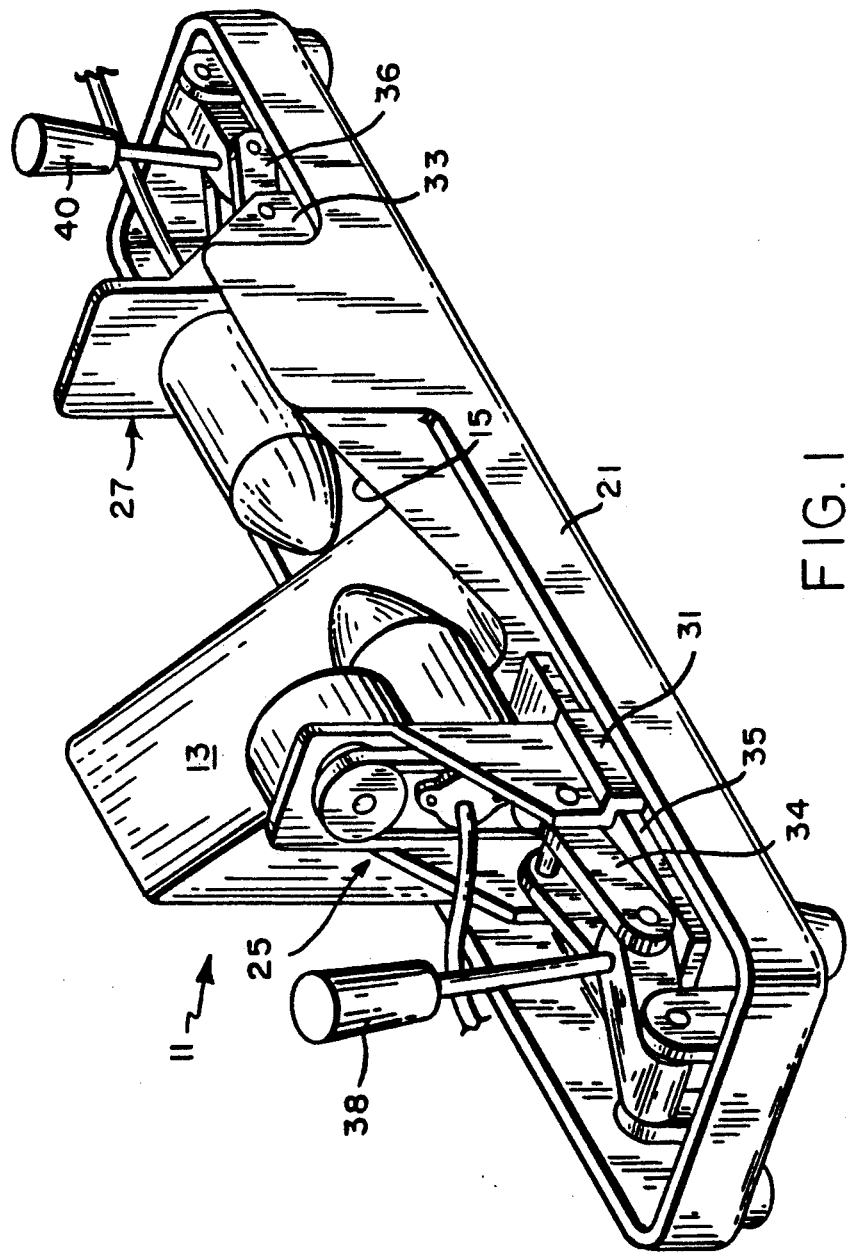
FIG. 1 is a prospective view of ultrasonic bone testing apparatus in accordance with the present invention.
Figure 2:
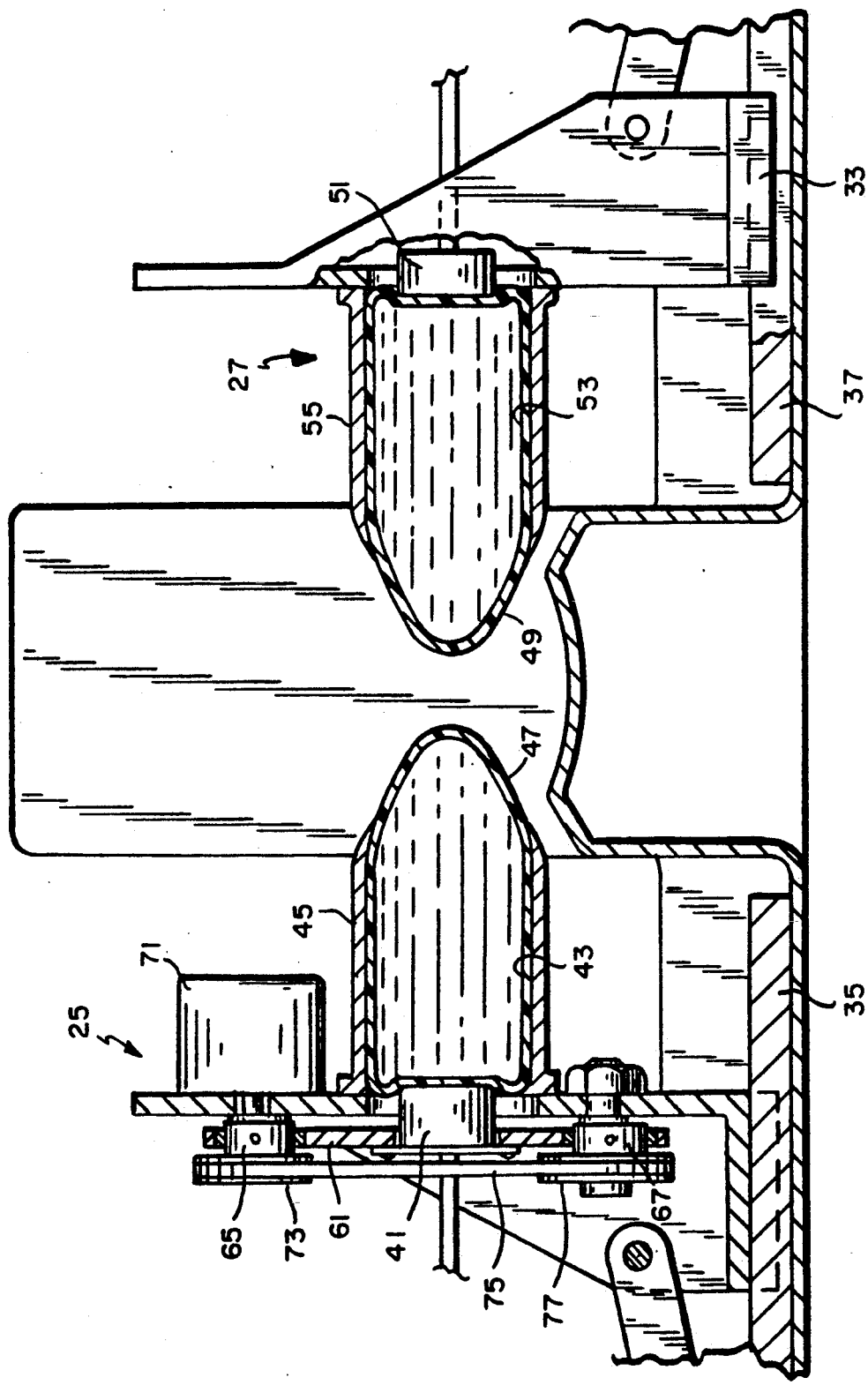
FIG. 2 is a sectional view from the rear of the apparatus of FIG. 1.
Figure 5:
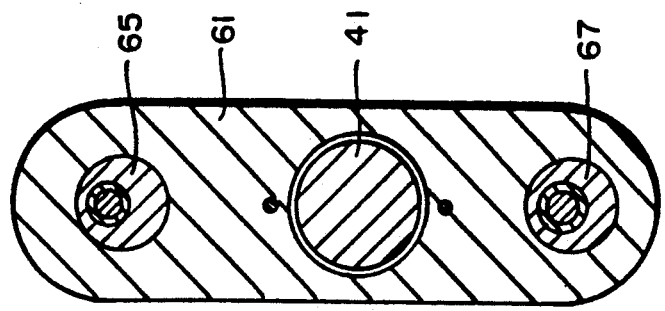
FIG. 5 is a sectional view of the scanning assembly taken essentially on the line A—A of FIG. 4.
Figure 4:
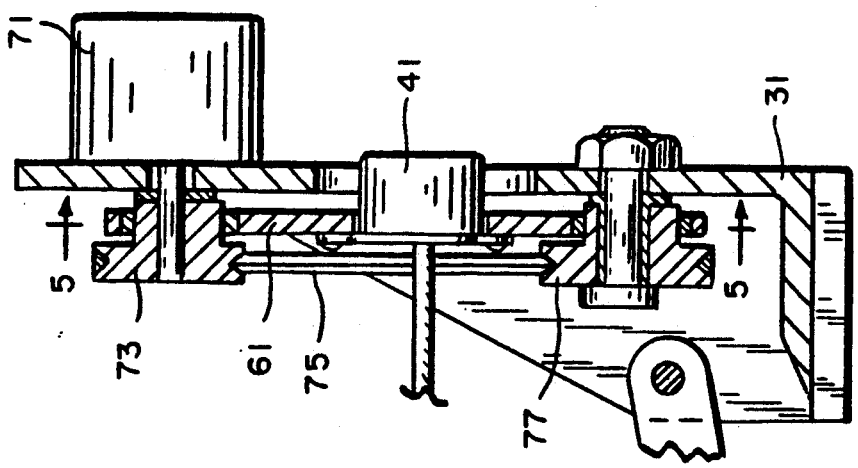
FIG. 4 is a sectional view from the rear of scanning assembly.
Figure 3:
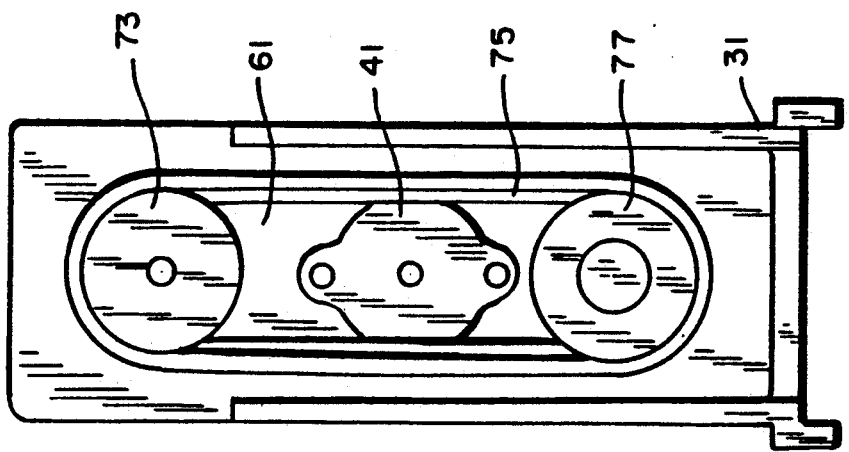
FIG. 3 is an end view of the apparatus of FIG. 1 showing a motor driven transducer scanning assembly employed therein.

Referring now particularly to FIGS. 1 and 2, the apparatus illustrated includes a footrest which is designated generally by reference character 11 and which includes a sole support surface 13 and a backrest surface 15. The footrest 11 together with the base of the machine, designated generally by reference character 21, may conveniently be constructed of a thermoplastic sheet material suitably molded and assembled for example by adhesive bonding.

Transducer assemblies, designated generally by reference characters 25 and 27, are provided on either side of the footrest. In the embodiment illustrated, the transducer assemblies are mounted on respective carriages 31 and 33 which are, in turn, slidable on rails 35 and 37 so that the transducer assemblies can be brought into and withdrawn from contact with the foot of a patient placed within the footrest 11. Preferably toggle linkage 34 and 36, by respective handles 38 and 40, are provided for controlling the travel of the transducer assemblies along their respective rails so that, during the actual ultrasonic testing, the assemblies are always the same distance apart.

The transducer assembly 25 includes a transmitting transducer 41 and, for coupling acoustic energy into a patient's foot, an acoustic waveguide or coupler in the form of a liquid filled bladder 43, a portion of which is held in a respective bladder housing 45. The transducer assembly 27 includes a receiving transducer 51 and, for coupling acoustic energy out of the patient's foot, an acoustic waveguide or coupler in the form of a liquid filled bladder 53, a portion of which is held in a respective housing 55. As used herein, the term liquid should be understood to include gels.

The foot engaging end of each bladder is formed in the shape of a laterally projected rounded cone, these portions being designated respectively by reference characters 47 and 49. These projecting portions extend through corresponding openings in the ends of the housings 45 and 55. These projecting portions in one sense resemble the shape of one end of a football and for each, the length of projection is roughly equal to the diameter of the base of the cone.

As the transducer assemblies are progressively brought into contact with opposite sides of a patient's foot positioned in the footrest 11, i.e. by driving the respective carriages towards each other along their respective rails, the conically shaped projecting portions of the liquid filled bladders initially contact a relatively small area of the foot. As the transducer assemblies advance, however, a progressively enlarging area of contact is established and, by virtue of this progressive enlargement, air is progressively excluded from the area of contact. In this way, a region of contact is established in which there is no entrapped air at the interface to interfere with the coupling of ultrasonic energy as would cause inconsistent measurements.

In accordance with an ancillary aspect of the present invention, one or both of the transducers is mechanically scannable over a small area so that the line of transmission varies over a correspondingly small region in the patient's foot. It has been found that a simple circular scanning movement is sufficient to obtain and establish a satisfactory sample within the patient's foot for consistent measurement.

To effect a small circular scanning motion of the transmitting transducer 41, it is mounted on a plate 61 whose position is controlled by a pair of eccentrics 65 and 67. Eccentric 65 is driven directly by a geared down motor 71. Motor 71 also drives a sprocket 73 whose motion is coupled, through a cogged belt 75, to a sprocket 77 which drives the lower eccentric 67. Accordingly, by selectively energizing the motor 71, the actual location of the transmitting transducer 41 may be moved in a circle lying in a plane essentially perpendicular to the line of acoustic transmission through the patient's foot and thus the center of this line may also be correspondingly scanned. The diameter of the circle of movement of the transducer can typically range from 0.050 to 0.500 inches. While scanning of the transmitting transducer has been shown by way of illustration, it should be understood that the receiving transducer likewise could be scanned either alone or in combination with scanning of the transmitting transducer.

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Ultrasonic bone testing apparatus comprising:
   locating means for holding a body member in position;
   an ultrasonic transducer assembly;
   means for mounting said transducer assembly in contact with a body member in said locating means, said mounting means being movable thereby to permit a body member to be placed in said locating means,
   said transducer assembly including a transducer and an acoustic waveguide which is interposed between the transducer and a body member in said locating means, said waveguide comprising a liquid filled bladder, the body member engaging end of said bladder being in the form of a laterally projecting rounded cone, the length of the projection being roughly equal to the diameter of the base of the cone, whereby air can be progressively excluded from an enlarging area of contact with a body member in said locating means as the transducer assembly is brought into contact with the body member.

2. Ultrasonic bone testing apparatus comprising:
   a footrest;
   a pair of ultrasonic transducer assemblies;
   respective means for mounting each of said pair of transducer assemblies, one on each side of a foot positioned in said footrest, at least one of said mounting means being movable laterally thereby to permit a foot to be initially placed in said footrest,
   each of said transducer assemblies including a transducer and an acoustic waveguide, each waveguide comprising a liquid filled bladder, the foot end of each bladder being in the form of a laterally projecting rounded cone, whereby air can be progressively excluded from an enlarging area of contact with a foot in said footrest as the transducer assemblies are brought into contact with opposite sides of the foot.

3. Apparatus as set forth in claim 2 including means for mechanically scanning one of the transducers with a circular motion in a plane essentially perpendicular to a line between the transducers.

4. Ultrasonic bone testing apparatus comprising:
   a footrest;
   a pair of ultrasonic transducer assemblies;
   respective means for mounting each of said pair of transducer assemblies, one on each side of the calcaneus of a foot positioned in said footrest, said mounting means being movable laterally of the foot thereby to permit a foot to be initially placed in said footrest,
   each of said transducer assemblies including a transducer and an acoustic waveguide which is interposed between the transducer and a foot in said footrest, each waveguide comprising a liquid filled bladder, the foot end of each bladder being in the form of a laterally projecting rounded cone, the length of the projection being roughly equal to the diameter of the base of the cone, whereby air can be progressively excluded from an enlarging area of contact with a foot in said footrest as the transducer assemblies are brought into contact with opposite sides of the foot.

5. Apparatus as set forth in claim 4 including means for mechanically scanning one of the transducers with a circular motion in a plane essentially perpendicular to a line between the transducers.

6. Ultrasonic bone testing apparatus comprising:
   a footrest;
   a pair of ultrasonic transducer assemblies;
   respective means for mounting each of said pair of transducer assemblies, one on each side of the calcaneus of a foot positioned in said footrest, said mounting means being movable laterally of the foot thereby to permit a foot to be initially placed in said footrest and to then permit the transducer assemblies to be brought into contact with the foot;
   each of said transducer assemblies including a transducer and a coupler which is interposed between the transducer and a foot in said footrest, each coupler comprising a liquid filled bladder, the foot end of each bladder being laterally projecting, thereby to exclude air from an area of contact with a foot in said footrest as the transducer assemblies are brought into contact with opposite sides of the foot with the transducers being a predetermined distance apart; and
   means for mechanically scanning at least one of the transducers with a circular motion in a plane approximately perpendicular to a line between the transducers.

* * * * *